US009568603B2

(12) United States Patent
Yahav et al.

(10) Patent No.: US 9,568,603 B2
(45) Date of Patent: Feb. 14, 2017

(54) EYEWEAR-MOUNTABLE EYE TRACKING DEVICE

(71) Applicant: Microsoft Technology Licensing, LLC, Redmond, WA (US)

(72) Inventors: Giora Yahav, Haifa (IL); David Cohen, Nesher (IL); Sagi Katz, Yokneam Ilit (IL)

(73) Assignee: Microsoft Technology Licensing, LLC, Redmond, WA (US)

( * ) Notice: Subject to any disclaimer, the term of this patent is extended or adjusted under 35 U.S.C. 154(b) by 77 days.

(21) Appl. No.: 14/610,984

(22) Filed: Jan. 30, 2015

(65) Prior Publication Data

US 2016/0139265 A1    May 19, 2016

Related U.S. Application Data

(63) Continuation of application No. 14/542,455, filed on Nov. 14, 2014, now abandoned.

(51) Int. Cl.
*G01J 3/00* (2006.01)
*G01S 17/06* (2006.01)
(Continued)

(52) U.S. Cl.
CPC ............... *G01S 17/06* (2013.01); *A61B 3/113* (2013.01); *G02B 27/0093* (2013.01);
(Continued)

(58) Field of Classification Search
CPC . G06F 3/013; G02B 27/0093; G06K 9/00604; A61B 3/113; G02C 11/10; G02C 11/04; G01S 17/06; G01S 17/66
See application file for complete search history.

(56) References Cited

U.S. PATENT DOCUMENTS

| 4,145,122 A | 3/1979 | Rinard et al. |
| 5,481,622 A | 1/1996 | Gerhardt et al. |

(Continued)

FOREIGN PATENT DOCUMENTS

WO        9733435 A1    9/1997

OTHER PUBLICATIONS

"International Search Report & Written Opinion Issued in PCT Application No. PCT/US2015/059803", Mailed Date: Feb. 4, 2016, 13 Pages.

(Continued)

*Primary Examiner* — Kara E Geisel
*Assistant Examiner* — Rufus Phillips
(74) *Attorney, Agent, or Firm* — Micah P. Goldsmith; Judy Yee; Micky Minhas

(57) ABSTRACT

An eye movement tracking device that can be mounted to standard eyeglasses as disclosed. The device comprises an illumination source, a time-of-flight (TOF) camera and a processor. The source transmits energy within a frequency band from a location proximate to an eye of a person, such that at least a first portion of the transmitted energy is reflected off a lens of eyewear worn by the person to subsequently reflect off the eye, and such that at least a second portion of the transmitted energy is transmitted through the lens to reflect off objects in the person's environment. The TOF camera detects reflections of at least the first portion of the transmitted energy, and distinguishes them from other energy detected by the TOF camera in said frequency band, based on TOF principles. The processor uses the detected reflections of the first portion of the transmitted energy to determine eye position.

9 Claims, 8 Drawing Sheets

(51) Int. Cl.
   *A61B 3/113*   (2006.01)
   *G06F 3/01*    (2006.01)
   *G06K 9/00*    (2006.01)
   *G02B 27/00*   (2006.01)
   *G02C 11/04*   (2006.01)
   *G02C 11/00*   (2006.01)

(52) U.S. Cl.
   CPC .............. *G02C 11/04* (2013.01); *G02C 11/10* (2013.01); *G06F 3/013* (2013.01); *G06K 9/00604* (2013.01)

(56) References Cited

U.S. PATENT DOCUMENTS

| | | |
|---|---|---|
| 6,637,883 B1 | 10/2003 | Tengshe et al. |
| 7,796,239 B2 | 9/2010 | Sawachi |
| 8,235,529 B1 | 8/2012 | Raffle et al. |
| 8,330,820 B2 | 12/2012 | Liberman et al. |
| 8,510,166 B2 | 8/2013 | Neven |
| 8,717,469 B2 | 5/2014 | Felzenshtein et al. |
| 2007/0014552 A1 | 1/2007 | Ebisawa |
| 2013/0135181 A1 | 5/2013 | Eberl et al. |
| 2013/0178287 A1 | 7/2013 | Yahav |
| 2013/0258112 A1 | 10/2013 | Baksht |
| 2014/0125766 A1 | 5/2014 | Cohen et al. |
| 2014/0184775 A1 | 7/2014 | Drake et al. |

OTHER PUBLICATIONS

Gwon, et al., "Gaze Tracking System for User Wearing Glasses", In Proceedings of Sensors, vol. 14, Issue 2, Jan. 27, 2014, 5 pages.
Bohme, et al., "Remote Eye Tracking: State of the Art and Directions for Future Development", In Proceedings of 2nd Conference on Communication by Gaze Interaction, Sep. 4, 2006, 2 pages.
Kassner, et al., "Pupil: An Open Source Platform for Pervasive Eye Tracking and Mobile Gaze-based Interaction", In Proceedings of CVPR, Aug. 25, 2014, 3 pages.
"Eye Tracking with Glasses", Published on: Sep. 26, 2011, http://www.mirametrix.com/eye-tracking-with-glasses/.
Bergasa, et al., "Real-Time System for Monitoring Driver Vigilance", In IEEE Transactions on Intelligent Transportation Systems, vol. 7, No. 1, Mar. 2006, pp. 63-77.
"Tobii Eye Tracking Glasses", Retrieved on: Aug. 26, 2014, http://imotionsglobal.com/portfolio-item/tobii-glasses/.
"An Introduction to Eye Tracking and Tobii Eye Trackers", Retrieved on: Sep. 8, 2014, http://www.tobii.com/en/eye-tracking-research/global/library/white-papers/tobii-eye-tracking-white-paper/.
Written Opinion of the International Preliminary Examining Authority mailed Oct. 12, 2016 for International Application No. PCT/US2015/059803. (9 pages).

EYEWEAR-MOUNTABLE EYE TRACKING DEVICE

This is a continuation of U.S. patent application Ser. No. 14/542,455, filed on Nov. 14, 2014, which is incorporated herein by reference in its entirety.

FIELD OF THE INVENTION

At least one embodiment of the present invention pertains to eye tracking technology, and more particularly, to an eye tracking device usable with standard eyeglasses.

BACKGROUND

Eye tracking (also called gaze tracking) technology is evolving to become an important part of next generation human-computer interfaces. Eye tracking technology has many potential applications in entertainment, research, and as an interaction tool for people who are physically impaired.

Most known video-based eye tracking systems use infrared (IR) cameras with IR light sources to detect the pupil/iris as well as glints from the illumination. Additionally, these systems generally use either direct imaging or indirect imaging. Direct imaging systems image the eye region directly by placing one or more IR sensors directly aimed at the eyes. These systems have problems, however, with occlusion of the sensor (e.g., from eyelashes) as well as the user's vision (e.g., from the sensor). These systems have particular trouble tracking the eyes of people who wear eyeglasses, at least partly because the eyeglasses cause occlusions or disturb the computer vision algorithms by creating false specular reflections.

Indirect imaging systems partly address the occlusion problem by viewing the eye via a so-called "hot mirror" lens, which acts as a mirror to near-IR limitation but as pass-through glass to visible light. In that way, the sensor can view the eye from a frontal position while avoiding occlusion of the user's field of view. However, the indirect imaging approach requires special glasses (i.e., equipped with hot mirror lenses) and, therefore, is not suitable for people who depend on standard (prescription) eyeglasses.

SUMMARY

The technology introduced here includes an eye tracking device that can be used to perform eye tracking for a user wearing standard eyeglasses. In at least some embodiments the device comprises an illumination source, a time-of-flight (TOF) camera and a processor. The illumination source transmits energy within a frequency band from a location proximate to an eye of a person, such that at least a first portion of the transmitted energy is reflected off a lens of eyewear worn by the person, to subsequently reflect off an eye of the person, and such that at least a second portion of the transmitted energy is transmitted through the lens to reflect off objects in the person's environment. The TOF camera detects reflections of at least the first portion of the transmitted energy, and distinguishes the detected reflections of the first portion of the transmitted energy from other energy detected by the TOF camera in said frequency band, based on times of flight of the reflections. The processor is configured to use the detected reflections of the first portion of the transmitted energy to determine a gaze direction of the eye of the person. Other aspects of the technique will be apparent from the accompanying figures and detailed description.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

One or more embodiments of the present invention are illustrated by way of example and not limitation in the figures of the accompanying drawings, in which like references indicate similar elements.

DETAILED DESCRIPTION

Figure 1A:
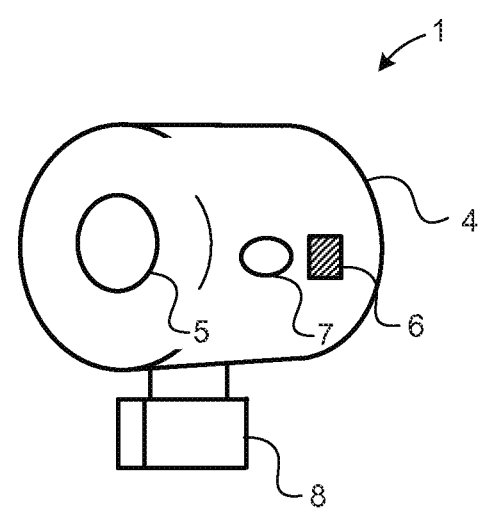
FIGS. 1A and 1B show perspective views of an eye tracking device according to an embodiment of the technology introduced here.

In this description, references to "an embodiment", "one embodiment" or the like, mean that the particular feature, function, structure or characteristic being described is included in at least one embodiment of the technique introduced here. Occurrences of such phrases in this specification do not necessarily all refer to the same embodiment. On the other hand, the embodiments referred to also are not necessarily mutually exclusive.

The technology introduced here includes an indirect imaging, eyewear-mounted eye tracking device that can be used to perform eye tracking for a user wearing standard eyeglasses. Note, however, that the device can also be used with other types of eyewear, such as special-purpose eyewear or headsets (e.g. for gaming or virtual/augmented reality applications). The device can be embodied as an add-on product that detachably mounts to standard (e.g., prescription) eyeglasses and that does not occlude the user's field of view. The device applies principles of TOF to its own IR illumination, to distinguish between desired IR energy (e.g., IR transmitted from its own source(s) and reflected off the eye of the user, which it uses for eye tracking) and undesired IR energy (e.g., ambient IR energy and IR that has been transmitted from its source(s) and reflected off objects in the user's environment).

In at least some embodiments the eye tracking device includes one or more IR illumination sources to emit IR energy; a gated "fast shutter" IR TOF camera (hereinafter simply "IR camera") synchronized with the IR source(s) to detect the emitted IR energy; a human-visible spectrum (e.g., red-green-blue (RGB)) video camera ("scene camera") to generate video of the general direction in which the user is looking during eye tracking and thereby enable marking of the user's point-of-regard (POR) on that video; a memory to store image data collected by the aforementioned cameras, a processing unit to compute the eye position of the user based on outputs of the IR camera (or at least a communication unit to enable communication with such a processing unit located external to the device); a housing to at least partially contain the aforementioned elements; and a fastener compatible with standard glasses, by which to mount the housing detachably to the frame of the eyeglasses.

In some embodiments, the device uses the fast-shutter IR camera, which employs an optical focusing system, to collect IR light reflected from nearby distances, namely, the user's eyes, and to avoid collecting ambient IR illumination and reflections of the device's own IR illumination from objects in the user's environment. This can be done by setting the shutter timing of the IR camera so that IR light transmitted from the device will be cut off by the shutter (which may be a purely electronic shutter) on its way back to the IR camera's sensor, so that only IR reflected or originating from objects from very nearby the sensor (e.g., within a few centimeters) is captured by the IR camera; that is, only energy with a sufficiently short TOF is allowed to be captured. This enables the IR camera to capture only the image of the eye, without reflections from outside objects. This feature, therefore, avoids the need to use a hot mirror. The IR camera is a "fast shutter" camera in that it can capture multiple images at nearly the same instant in time, by closing and opening its "shutter" (e.g., an electronic shutter) repeatedly within a very short period of time, e.g., every few nanoseconds.

One type of IR camera that can be used for this purpose is a "gated" TOF depth camera. A gated TOF depth camera utilizes a series of light pulses in order to illuminate a scene imaged by the depth camera. For each light pulse, the depth camera is "gated" ON for a particular exposure period before being "gated" OFF again, thereby imaging the scene during the exposure period. A distance to a feature in the scene may be determined from an amount of light from the transmitted pulses that is reflected by the feature and registered by a pixel of the camera sensor during the exposure period. A pulsed IR TOF depth camera of this type can be used. Alternately, a TOF camera that uses the principle of phase modulation may also be usable for this purposes of the technique introduced here.

Additionally, the device can acquire two or more such IR images at nearly the same time using different illumination settings, to filter out ambient IR illumination and/or to identify different specular reflections from the eye (glints). This feature enables the device to perform ambient-invariant eye tracking, i.e., allows it to function properly in environments with uncontrolled ambient illumination. The device can also compute depth (using TOF principles) for use in gesture recognition and/or other applications.

Figure 1B:
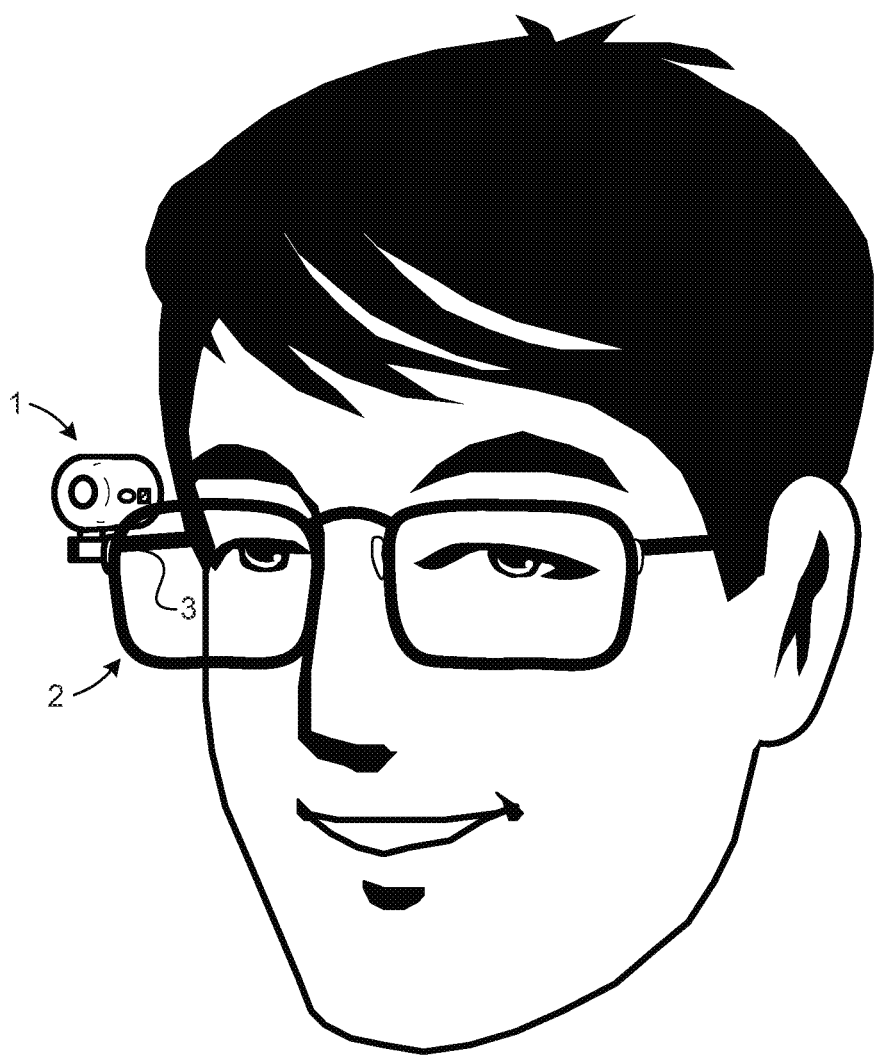

FIGS. 1A and 1B illustrate the eyeglasses-mounted eye tracking device according to at least one embodiment. As shown, the eye tracking device 1 can be mounted to the frame of standard eyeglasses 2 (FIG. 1B), such as to either one of the two temple frame pieces 3, proximate to one of the user's eyes. "Proximate" in this context means within a few centimeters, such as less than about 5 cm. Note that the physical shape of the device 1 as shown in FIG. 1 is just one of many possible examples of the shape the eye tracking device may have. As discussed further below, the device 1 has a housing 4, which at least partially contains a forward-looking human-visible spectrum video camera 5 (e.g., an RGB video camera), at least one near-IR illumination source 6 and a gated "fast shutter" IR camera that includes an IR sensor 7. The device further includes a fastener 8 (e.g., a spring-loaded clip, Velcro, or the like) to detachably connect the device 1 to the eyeglasses frame 3. The fastener 8 can be a "universal" fastener capable of mounting the device to any standard eyeglasses, or it can be designed specifically for a given model or manufacturer's eyeglasses.

Figure 2:
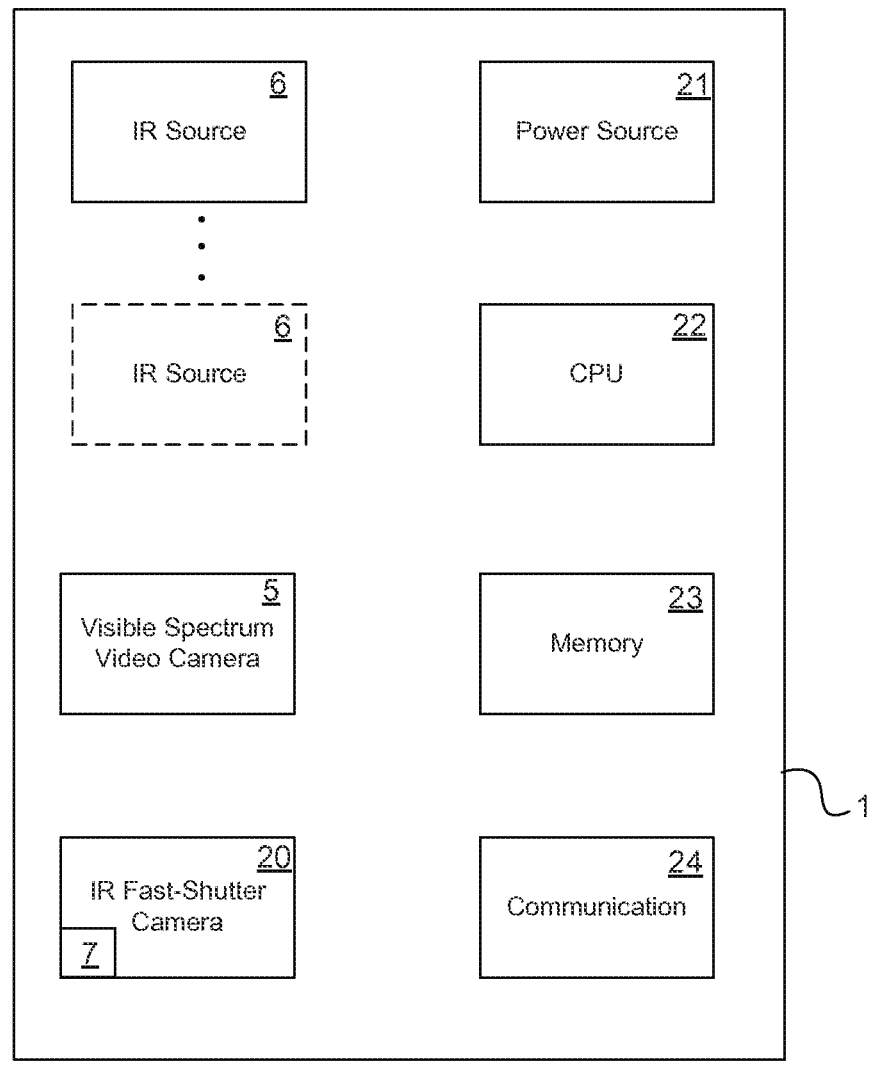
FIG. 2 is a block diagram showing functional elements of an embodiment of the eye tracking device.

FIG. 2 is a block diagram further illustrating showing these and other elements of an embodiment of the eye tracking device according to at least one embodiment. As illustrated the device 1 includes a power source 21 (e.g., a battery), a central processing unit (CPU) 22, memory 23, a gated "fast shutter" IR camera 20 including the IR sensor 7, the one or more IR illumination sources 6, the human-visible spectrum video camera ("scene camera") 5, and a communication unit 24. The device 1 further includes lenses (not shown) associated with the IR cameras.

The scene camera 5 can be any conventional video camera. The IR camera 20 can be a fast shutter gated TOF IR camera that has a resolution in its depth measurements to within a few centimeters. Note that in some embodiments, the IR camera 20 may include its own processor and/or memory (not shown), separate from the CPU 22 and memory 23, for performing image capture and/or image processing operations.

In some embodiments, the CPU 22 controls operation of the other components of the device 1 and determines gaze direction or performs eye tracking computations related to gaze determinations. The CPU 22 can be or include any known or convenient form of processor and/or controller, such as an appropriately programmed general-purpose microprocessor, special-purpose microprocessor or digital signal processor, programmable microcontroller, application-specific integrated circuit (ASIC), programmable logic device (PLD), or the like, or a combination of any two or more such devices. Further, if the CPU 22 is a programmable microprocessor, it can be either a single-core processor or a multicore processor.

The memory 23 can be used to store any one or more of: the image data acquired by the IR camera, the image data acquired by the visible spectrum, program code for execution by the CPU, intermediate data resulting from computations or calculations by the CPU, or other data and/or program code. Hence, portions of memory 23 can actually reside in the CPU 22, the visible spectrum camera 5 or the IR camera 20. Memory 23 can be include one or more physical storage devices, which may be or include random access memory (RAM), read-only memory (ROM) (which may be erasable and programmable), flash memory, miniature hard disk drive, or other suitable type of storage device, or a combination of such devices.

The communication unit 24 enables the eye tracking device 1 to communicate with an external device or system (not shown), such as a computer or other type of processing device. For example, in certain embodiments, at least some of the eye tracking computations may be done by an external device (e.g., a personal computer), based on data acquired by the eye tracking device and transmitted to the external device by the communication unit. This may allow the programming or configuration of the CPU 22 to be made much simpler, or it may allow the CPU 22 to be replaced by a much simpler type of controller, or even omitted entirely from the eye tracking device 1. The communication unit 24 can be or include a transceiver that performs wired communication, wireless communication, or both. For example, the communication unit 24 can be or include any one or more of: a universal serial bus (USB) adapter, Ethernet adapter, modem, Wi-Fi adapter, cellular transceiver, baseband processor, Bluetooth or Bluetooth Low Energy (BLE) transceiver, or the like, or a combination thereof.

Each IR source 6 of the device can be or include, for example, one or more light emitting diodes (LEDs) or diffused laser sources. Laser sources can be used in conjunction with TOF principles to provide high quality depth determination, such as for use in gesture recognition. As discussed further below, the illumination by the IR source(s) 6 is controlled such that for each shutter window of an imaging frame, the illumination can be set on or off. For embodiments in which there is more than one IR source 6, the device 1 is able to turn on or off each source independently.

Figure 3:
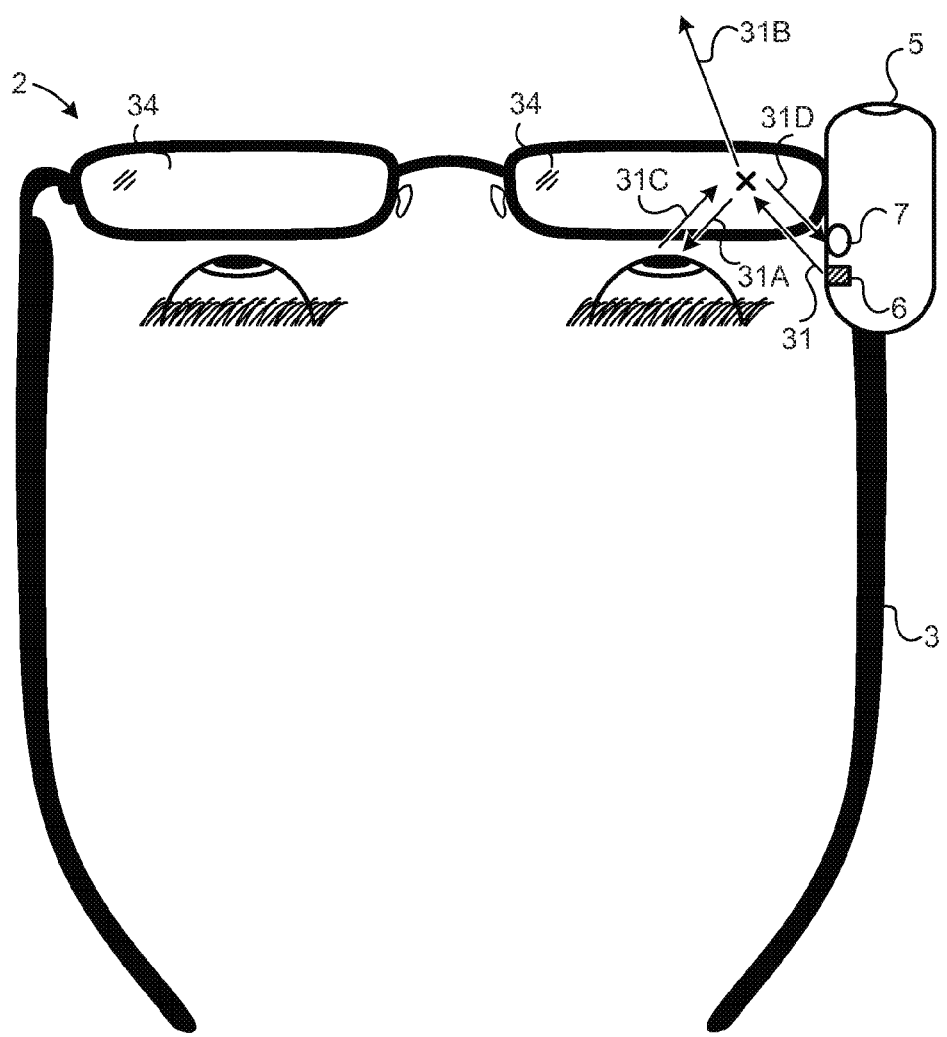
FIG. 3 shows an example of the eye tracking device mounted on a pair of standard eyeglasses.
Figure 4:
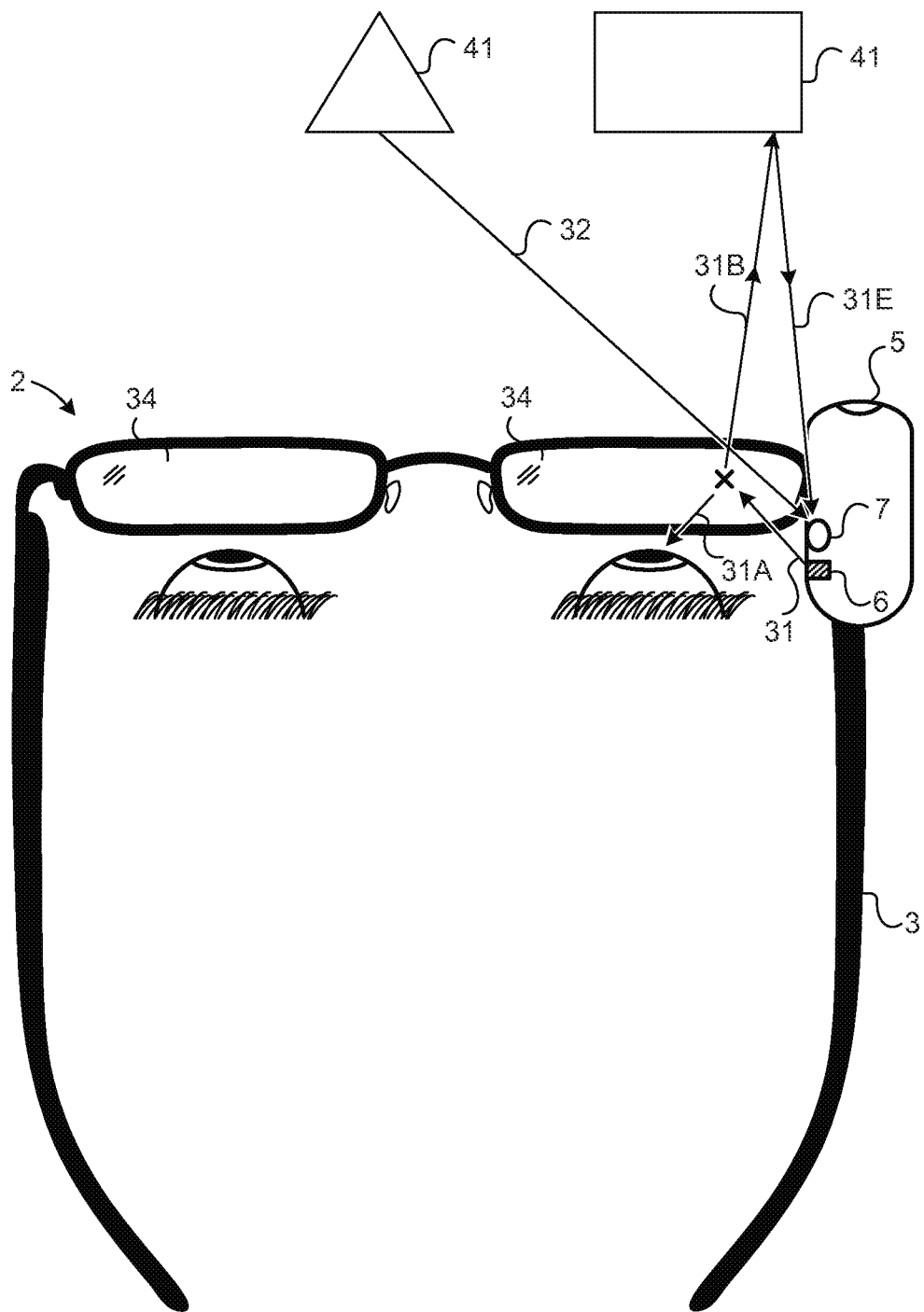
FIG. 4 schematically illustrates the propagation of IR illumination in a typical usage scenario.

FIGS. 3 and 4 illustrate the principle of operation of the eye tracking device, according to at least one embodiment. Note that FIG. 3 is intended to be schematic in nature, such that the actual positions of the source 6 and sensor 7 in an actual implementation may differ from their positions as shown in FIG. 3. The IR source 6 transmits IR energy at an angle toward one of the lenses 34 of the eyeglasses 2. As mentioned above, the eyeglasses 2 are assumed to be standard eyeglasses, such that the lens is made of standard optometric-quality glass or any other material suitable for standard eyeglass lenses. A portion 31A of the transmitted IR energy 31 (typically about 5% of it, with glass) is reflected off the inner surface of the nearest lens 34 to reach an eye 32 of the user. The remaining portion 31B (typically about 95% of it, with glass) of the transmitted IR energy 31 is transmitted completely through the lens to the user's environment. As shown in FIG. 3, at least a portion 31C of the IR energy that reaches the user's eye is reflected off the cornea back to the inner surface of the lens, where a portion 31D of that remaining energy is further reflected back to the sensor 7 of the IR camera (not fully shown in FIGS. 3 and 4). The IR energy 31D that reaches the IR sensor 7 is detected and used by the CPU 22 (or alternatively by an external device) to determine the eye position (i.e., using pupil and/or iris identification). Once the eye position is determined, it is possible to identify the gaze location on the RGB video image by using standard methods for gaze tracking. One way to accomplish this is by using a polynomial to map the pupil center or the pupil-glint vector to the RGB coordinates.

Further, at least a portion 31E (FIG. 4) of the IR energy 31B that was transmitted through the lens to the user's environment is reflected off objects 41 in the environment back to the IR sensor 7, as shown. Additionally, ambient IR energy 32 in the environment (e.g., from objects 41) may also reach the IR sensor 7. However, the fast shutter and TOF principles of the IR camera 20 enable the eye tracking device 1 to filter out all of that IR energy except the portion 31D of IR energy reflected from the user's eye that reaches the sensor 7. This can be done by setting the shutter timing of the IR camera 20 so that IR energy transmitted from the device 1 will be cut off by the shutter (which may be electronic) on its way back to the IR camera's sensor 7, so that only IR reflected or originating from objects from very nearby the sensor 7 (e.g., within a few centimeters) is captured by the IR camera 20; that is, only energy with a sufficiently short TOF is allowed to be captured. This enables the IR camera 20 to capture only the image of the eye, without reflections from outside objects.

Further, by using multiple shutter (time) windows within each imaging frame, it is possible to eliminate reflections from IR light that did not originate from the device 1, i.e., to filter out ambient IR. One way to do that is to subtract a non-illuminated image acquired during one shutter window from an IR-illuminated image acquired during an immediately preceding or immediately following shutter window.

Figure 5:
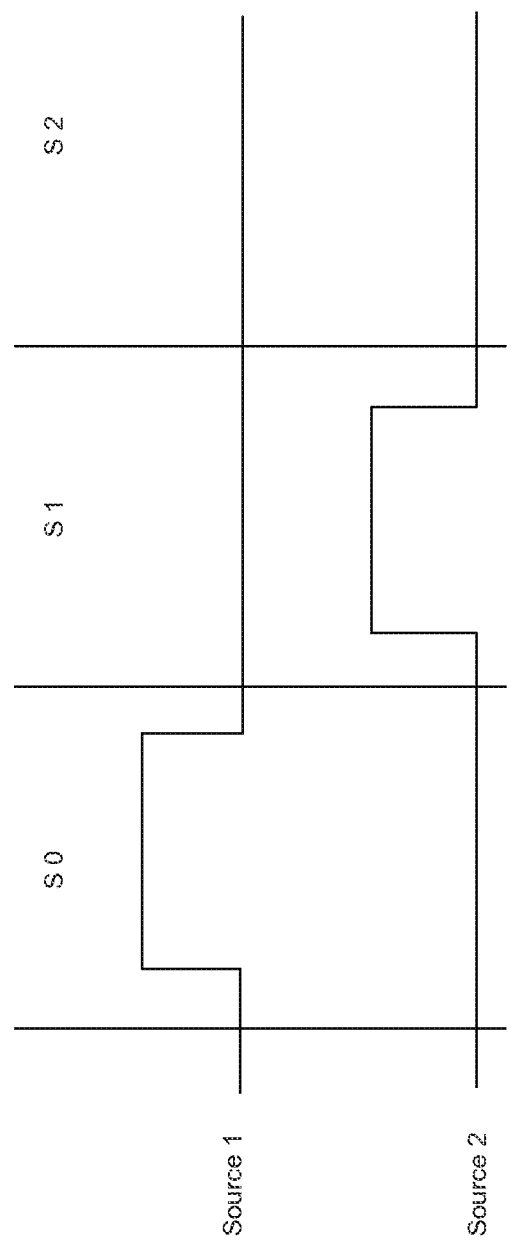
FIG. 5 illustrates an example of an IR illumination scheme for an embodiment with two illumination sources.

Moreover, by using more than one illuminated shutter window per imaging frame, with different IR sources being active during different consecutive shutter windows in each frame, the device 1 can perform or enable robust glint and pupil identification (glint detection can be used for gaze stabilization to allow camera movement on the head without compromising the accuracy of the gaze determination). FIG. 5 illustrates this principle, for an example IR illumination scheme that uses two IR sources 6, called Source 1 and Source 2. In the illustrated scheme, the IR camera uses three shutter windows per imaging frame, i.e., shutters windows S0, S1 and S2, where the IR sources are controlled (e.g., by the CPU 22) to be synchronized to the shutter windows, as follows: During shutter window S0, Source 1 is on and Source 2 is off; during shutter window, S1, source S2 is on and source 1 is off; and during shutter window S2, both IR sources are off. Source 1 and source 2 each produce a separate specular reflection from a different position on the eye, which can be used for accurate glint and pupil identification. Hence, the IR camera 20 in this embodiment actually captures three independent images per imaging frame, one for each shutter window, all corresponding to essentially the same instant in time (i.e., the same at least for purposes of gaze tracking). Those separate images per frame are separately stored in memory 23 and are independently retrievable to allow processing as described above.

Figure 6:
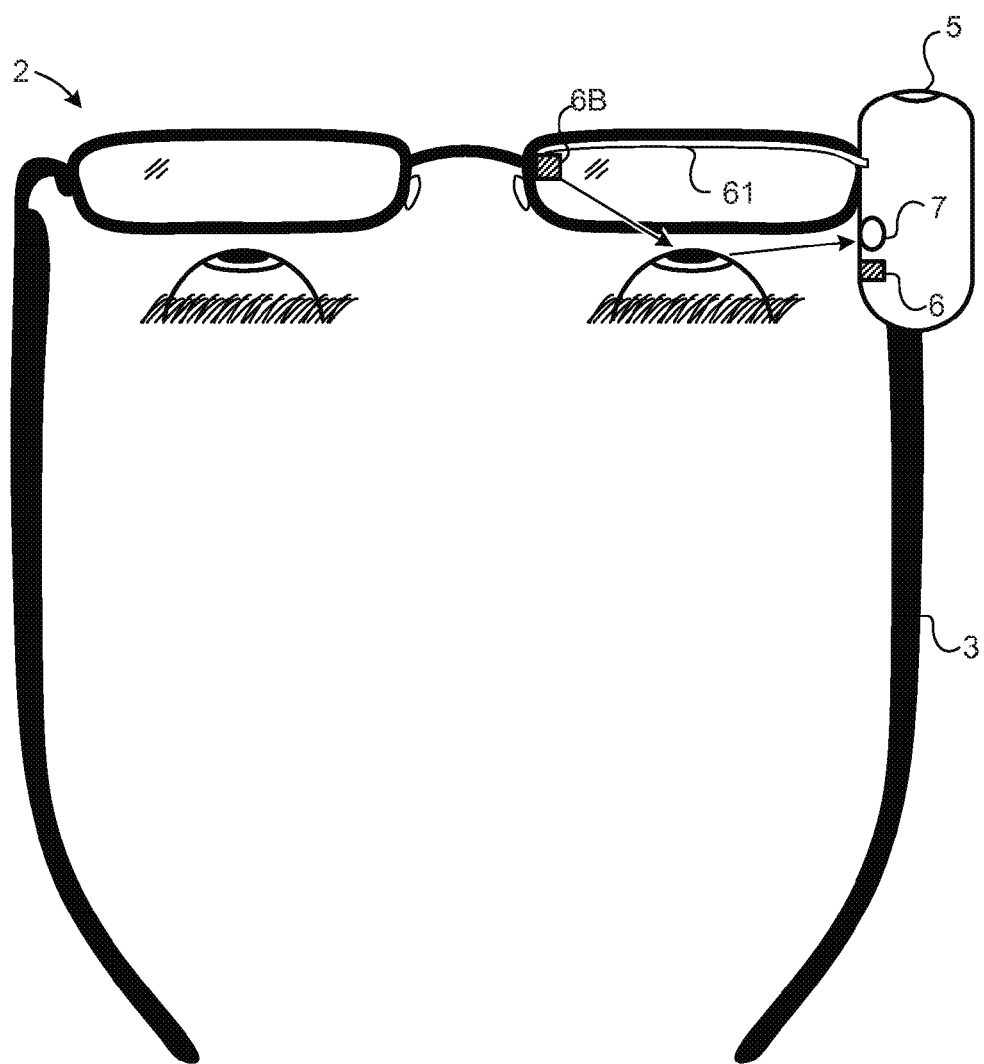
FIG. 6 illustrates an embodiment of the eye tracking device with two illumination sources.

FIG. 6 shows an embodiment of the eye tracking device with two illumination sources. A second IR source 6B can be positioned on or near the eyeglasses frame 3 proximate to the bridge of user's nose, for example. The second IR source 6B can be connected to the housing of the device by a connector 61 such as a wire, which may be rigid or semi-rigid to enable it to conform to the contour of the lens frame, or by any other suitable connection mechanism.

Figure 7:
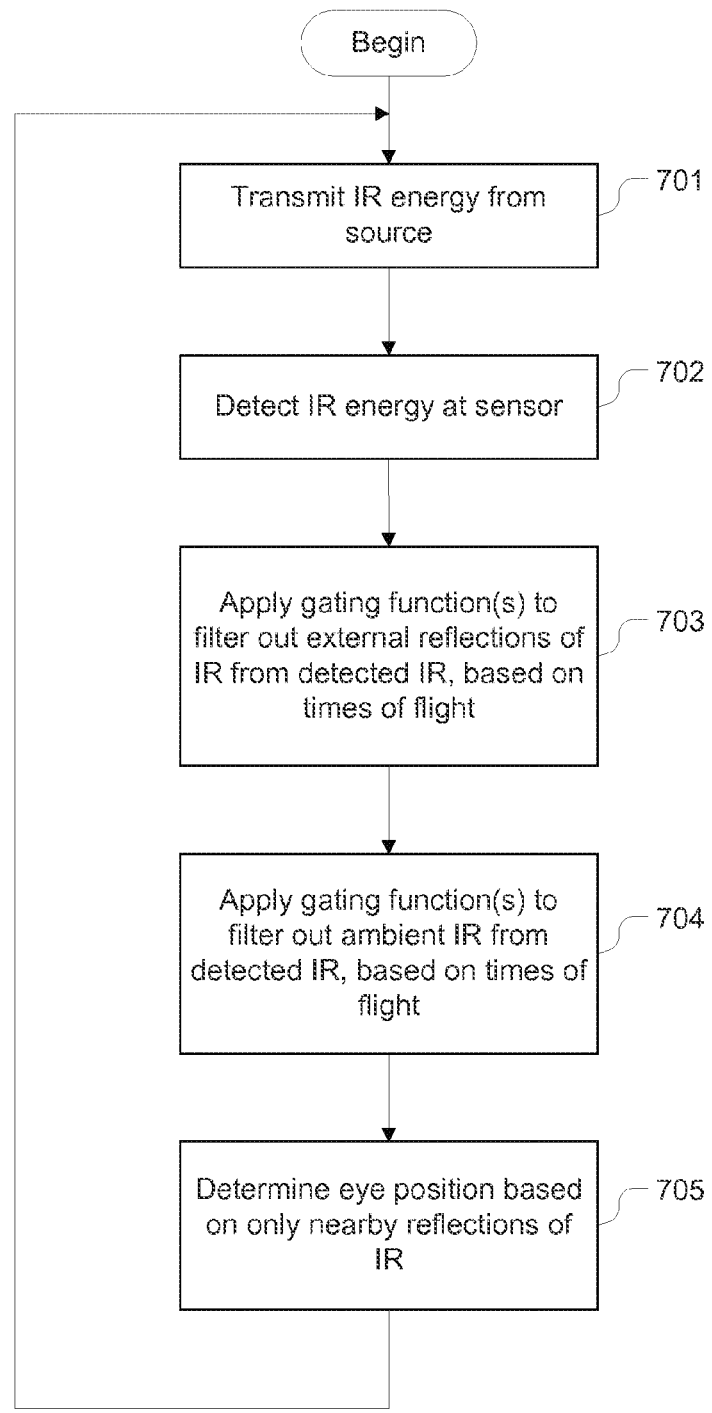
FIG. 7 is a flow diagram showing an example of the operational process of the eye tracking device.

FIG. 7 is a flow diagram showing an example of the operational process of the eye tracking device, according to some embodiments. At step 701 the device 1 transmits IR energy from an IR source 6. At step 702 the IR sensor 7 of the fast shutter IR camera 20 detects infrared energy. The IR camera 20 then applies one or more gating functions at step 703 to filter out external reflections of IR from the detected IR, based on their TOFs. The IR camera 20 further applies one or more gating functions at step 704 to filter out ambient IR from the detected IR, based on their TOFs. The CPU 23 then determines at step 705 the eye position of the user, based on only the nearby reflections of IR energy, e.g., reflections from the user's eye.

The machine-implemented operations described above can be implemented by programmable circuitry programmed/configured by software and/or firmware, or entirely by special-purpose circuitry, or by a combination of such forms. Such special-purpose circuitry (if any) can be in the form of, for example, one or more application-specific integrated circuits (ASICs), programmable logic devices (PLDs), field-programmable gate arrays (FPGAs), system-on-a-chip systems (SOCs), etc.

Software or firmware to implement the techniques introduced here may be stored on a machine-readable storage medium and may be executed by one or more general-purpose or special-purpose programmable microprocessors. A "machine-readable medium", as the term is used herein, includes any mechanism that can store information in a form accessible by a machine (a machine may be, for example, a computer, network device, cellular phone, personal digital assistant (PDA), manufacturing tool, any device with one or more processors, etc.). For example, a machine-accessible medium includes recordable/non-recordable media (e.g., read-only memory (ROM); random access memory (RAM); magnetic disk storage media; optical storage media; flash memory devices; etc.), etc.

Examples of Certain Embodiments

Certain embodiments of the technology introduced herein are as summarized in the following numbered examples:

1. An eye movement tracking device comprising: a first illumination source to transmit energy within a frequency band from a location proximate to an eye of a person, such that at least a first portion of the transmitted energy is reflected off a lens of eyewear worn by the person to subsequently reflect off the eye of the person and such that at least a second portion of the transmitted energy is transmitted through the lens to reflect off objects in an environment of the person; a time-of-flight detector to detect reflections of at least the first portion of the transmitted energy, and to distinguish the detected reflections of the first portion of the transmitted energy from other energy detected by the time-of-flight detector in said frequency band, based on times of flight of the reflections of the first portion of the transmitted energy and said other energy; and a processor configured to use the detected reflections of the first portion of the transmitted energy to determine a position of the eye of the person.

2. An eye movement tracking device according to example 1, further comprising a fastener by which the eye movement tracking device can be detachably mounted to standard eyeglasses.

3. An eye movement tracking device according to either of examples 1 and 2, wherein the transmitted energy is infrared energy.

4. An eye movement tracking device according to any of examples 1 through 3, further comprising a human-visible spectrum camera to capture images of a scene corresponding to a gaze direction of the person.

5. An eye movement tracking device according to any of examples 1 through 4, further comprising a second illumination source.

6. An eye movement tracking device according to any of examples 1 through 5, wherein the first illumination source is controlled to transmit energy during a first shutter window of an imaging frame and not to transmit energy during a second shutter window of the imaging frame; and wherein the processor is further configured to: identify ambient energy in the environment based on a difference between energy detected by the time-of-flight detector during the first shutter window and energy detected by the time-of-flight detector during the second shutter window; and filter out the ambient energy so that determination of the gaze direction of the eye is not affected by the ambient energy.

7. An eye movement tracking device according to any of examples 1 through 6, wherein the first and second shutter windows do not overlap.

8. An eye movement tracking device according to any of the preceding examples 1 through 7, further comprising a second illumination source controlled to transmit energy during a third shutter window of the imaging frame, wherein the first illumination source does not transmit during the third shutter window and the second illumination source does not transmit during the first shutter window.

9. An eye movement tracking device according to any of examples 1 through 8, wherein the processor is further configured to: distinguish energy detected by the sensor during the first shutter window from energy detecting by the sensor during the third shutter window; and identify corneal glints from the eye based on a difference between the energy detected by the sensor during the first shutter window and the energy detected by the sensor during the third shutter window.

10. An eye movement tracking device according to any of examples 1 through 9, wherein the processor is configured to perform gaze stabilization based on the corneal glints.

11. A method of tracking eye movement of a person, the method comprising: transmitting energy from a first source located proximate to an eye of the person, so that at least a first portion of the transmitted energy is reflected off an inner surface of a lens of eyewear worn by the person and at least a second portion of the transmitted energy is transmitted through the lens to reflect off objects in an environment of the person; detecting, by a sensor, reflections of both the first portion and the second portion of the transmitted energy; using corresponding times of flight of the first and second portions of the transmitted energy to distinguish detected reflections of the first portion of the transmitted energy from detected reflections of the second portion of the transmitted energy; and determining a gaze direction of the eye by using the detected reflections of the first portion of the transmitted energy and not the detected reflections of the second portion of the transmitted energy.

12. A method according to example 11, wherein said transmitting and said detecting are performed by an apparatus removably mounted to the eyewear worn by the person.

13. A method according to either of the preceding examples 11 and 12, wherein the energy transmitted from the first source comprises electromagnetic energy in an infrared portion of the electromagnetic spectrum and does not include energy in the human-visible portion of the electromagnetic spectrum.

14. A method according to any of examples 11 through 13, wherein the eyewear comprises conventional prescription eyewear, and the source and the detector are removably mounted to the eyewear.

15. A method according to any of examples 11 through 14, wherein the transmitted energy comprises infrared light and does not include energy in a human-visible portion of the electromagnetic spectrum.

16. A method according to any of examples 11 through 15, wherein said transmitting energy from the first source comprises transmitting energy from the first source during a first shutter window in each of a plurality of sequential imaging frames; wherein the first source does not transmit during a second shutter window in each of the plurality of sequential imaging frames; and the method further comprising: identifying ambient energy in the environment based on a difference between energy detected by the sensor during the first shutter window and energy detected by the sensor during the second shutter window in each of the plurality of imaging frames; and filtering out the ambient energy so that said determining the gaze direction of the eye is not affected by the ambient energy.

17. A method according to any of examples 11 through 16, wherein the first and second shutter windows do not overlap.

18. A method according to any of examples 11 through 17, further comprising: transmitting energy from a second source during a third shutter window in each of the plurality of sequential imaging frames; wherein the first source does not transmit during the third shutter window and the second source does not transmit during the first shutter window, in each of the plurality of sequential imaging frames; the method further comprising: distinguishing energy detected by the sensor during the first shutter window from energy detecting by the sensor during the third shutter window, in at least one of the plurality of sequential imaging frames; and identifying corneal glints from the eye based on a difference between the energy detected by the sensor during the first shutter window and the energy detected by the sensor during the third shutter window, in said at least one of the plurality of imaging frames, wherein determining the gaze direction of the eye includes using the corneal glints.

19. A method of tracking eye movement, the method comprising: transmitting only infrared light, from a first source mounted on eyeglasses worn by a person, so that at least a first portion of the transmitted infrared light is reflected off an inner surface of a lens of the eyeglasses and subsequently reflected off an eye of the person, and at least a second portion of the transmitted infrared light is transmitted through the lens to reflect off objects in an environment in which the person is located; detecting, by a sensor mounted on the eyeglasses worn by the person, reflections of both the first portion transmitted infrared light reflected off the eye of the person and the second portion of the transmitted infrared light reflected off objects in the environment; determining corresponding times of flight of the detected reflections of the first and second portions of the transmitted light; filtering out detected reflections of the second portion of the transmitted infrared light based on times of flight of the detected reflections of the first and second portions of the transmitted infrared light; filtering out ambient infrared light from light detected by the sensor; and tracking positions of the eye based on filtered outputs of the sensor, by using the detected reflections of the first portion of the transmitted infrared light.

20. A method according to example 19, wherein said transmitting infrared light from the first source comprises transmitting infrared light from the first source during a first shutter window in each of a plurality of sequential imaging frames; and wherein the first source does not transmit during a second shutter window in each of the plurality of sequential imaging frames, and wherein the first and second shutter windows do not overlap.

21. A method according to either of examples 19 and 20, further comprising:
transmitting infrared light from a second source during a third shutter window in each of the plurality of sequential imaging frames, wherein the first source does not transmit during the third shutter window and the second source does not transmit during the first shutter window, in each of the plurality of sequential imaging frames; identifying the ambient energy in the environment based on a difference between energy detected by the sensor during the first shutter window and energy detected by the sensor during the second shutter window, in each of the plurality of imaging frames; distinguishing energy detected by the sensor during the first shutter window from energy detecting by the sensor during the third shutter window, in at least one of the plurality of sequential imaging frames; and identifying corneal glints from the eye based on a difference between the energy detected by the sensor during the first shutter window and the energy detected by the sensor during the third shutter window, in said at least one of the plurality of imaging frames, wherein said tracking positions of the eye includes performing gaze stabilization based on the corneal glints.

22. A device for tracking eye movement of a person, the device comprising: means for transmitting energy from a first source located proximate to an eye of the person, so that at least a first portion of the transmitted energy is reflected off an inner surface of a lens of eyewear worn by the person and at least a second portion of the transmitted energy is transmitted through the lens to reflect off objects in an environment of the person; detecting, by a sensor, reflections of both the first portion and the second portion of the transmitted energy; means for using corresponding times of flight of the first and second portions of the transmitted energy to distinguish detected reflections of the first portion of the transmitted energy from detected reflections of the second portion of the transmitted energy; and means for determining a gaze direction of the eye by using the detected reflections of the first portion of the transmitted energy and not the detected reflections of the second portion of the transmitted energy.

23. A device according to example 22, wherein the device is removably mountable to the eyewear worn by the person.

24. A device according to either of the preceding examples 22 and 23, wherein the energy transmitted from the first source comprises electromagnetic energy in an infrared portion of the electromagnetic spectrum and does not include energy in the human-visible portion of the electromagnetic spectrum.

25. A device according to any of examples 22 through 24, wherein the eyewear comprises conventional prescription eyewear, and the source and the detector are removably mounted to the eyewear.

26. A device according to any of examples 22 through 25, wherein the transmitted energy comprises infrared light and does not include energy in a human-visible portion of the electromagnetic spectrum.

27. A device according to any of examples 22 through 26, wherein said means for transmitting energy from the first source comprises means for transmitting energy from the first source during a first shutter window in each of a plurality of sequential imaging frames; wherein the first source does not transmit during a second shutter window in each of the plurality of sequential imaging frames; and the device further comprising: means for identifying ambient energy in the environment based on a difference between energy detected by the sensor during the first shutter window and energy detected by the sensor during the second shutter window in each of the plurality of imaging frames; and means for filtering out the ambient energy so that said determining the gaze direction of the eye is not affected by the ambient energy.

28. A device according to any of examples 22 through 27, wherein the first and second shutter windows do not overlap.

29. A device according to any of examples 22 through 28, further comprising: means for transmitting energy from a second source during a third shutter window in each of the plurality of sequential imaging frames; wherein the first source does not transmit during the third shutter window and the second source does not transmit during the first shutter window, in each of the plurality of sequential imaging frames; the device further comprising: means for distinguishing energy detected by the sensor during the first shutter window from energy detecting by the sensor during the third shutter window, in at least one of the plurality of sequential imaging frames; and means for identifying corneal glints from the eye based on a difference between the energy detected by the sensor during the first shutter window and the energy detected by the sensor during the third shutter window, in said at least one of the plurality of imaging frames, wherein determining the gaze direction of the eye includes using the corneal glints.

30. A device of tracking eye movement, the device comprising: means for transmitting only infrared light, from a first source mounted on eyeglasses worn by a person, so that at least a first portion of the transmitted infrared light is reflected off an inner surface of a lens of the eyeglasses and subsequently reflected off an eye of the person, and at least a second portion of the transmitted infrared light is transmitted through the lens to reflect off objects in an environment in which the person is located; means for detecting, by a sensor mounted on the eyeglasses worn by the person, reflections of both the first portion transmitted infrared light reflected off the eye of the person and the second portion of the transmitted infrared light reflected off objects in the environment; means for determining corresponding times of flight of the detected reflections of the first and second portions of the transmitted light; means for filtering out detected reflections of the second portion of the transmitted infrared light based on times of flight of the detected reflections of the first and second portions of the transmitted infrared light; means for filtering out ambient infrared light from light detected by the sensor; and tracking positions of the eye based on filtered outputs of the sensor, by using the detected reflections of the first portion of the transmitted infrared light.

31. A device according to example 30, wherein said means for transmitting infrared light from the first source comprises means for transmitting infrared light from the first source during a first shutter window in each of a plurality of sequential imaging frames; and wherein the first source does not transmit during a second shutter window in each of the plurality of sequential imaging frames, and wherein the first and second shutter windows do not overlap.

32. A device according to either of examples 30 and 31, further comprising:
means for transmitting infrared light from a second source during a third shutter window in each of the plurality of sequential imaging frames, wherein the first source does not transmit during the third shutter window and the second source does not transmit during the first shutter window, in each of the plurality of sequential imaging frames; means for identifying the ambient energy in the environment based on a difference between energy detected by the sensor during the first shutter window and energy detected by the sensor during the second shutter window, in each of the plurality of imaging frames; means for distinguishing energy detected by the sensor during the first shutter window from energy detecting by the sensor during the third shutter window, in at least one of the plurality of sequential imaging frames; and means for identifying corneal glints from the eye based on a difference between the energy detected by the sensor during the first shutter window and the energy detected by the sensor during the third shutter window, in said at least one of the plurality of imaging frames, wherein said tracking positions of the eye includes using the corneal glints to perform gaze stabilization.

Any or all of the features and functions described above can be combined with each other, except to the extent it may be otherwise stated above or to the extent that any such embodiments may be incompatible by virtue of their function or structure, as will be apparent to persons of ordinary skill in the art. Unless contrary to physical possibility, it is envisioned that (i) the methods/steps described herein may be performed in any sequence and/or in any combination, and that (ii) the components of respective embodiments may be combined in any manner.

Although the subject matter has been described in language specific to structural features and/or acts, it is to be understood that the subject matter defined in the appended claims is not necessarily limited to the specific features or acts described above. Rather, the specific features and acts described above are disclosed as examples of implementing the claims and other equivalent features and acts are intended to be within the scope of the claims.

What is claimed is:
1. A method of tracking eye movement, the method comprising:
transmitting only infrared light, from a first source mounted on eyeglasses worn by a person, so that at least a first portion of the transmitted infrared light is reflected off an inner surface of a lens of the eyeglasses and subsequently reflected off an eye of the person, and at least a second portion of the transmitted infrared light is transmitted through the lens to reflect off objects in an environment in which the person is located;
detecting, by a sensor mounted on the eyeglasses worn by the person, reflections of both the first portion transmitted infrared light reflected off the eye of the person and the second portion of the transmitted infrared light reflected off objects in the environment;
determining corresponding times of flight of the detected reflections of the first and second portions of the transmitted light;
filtering out detected reflections of the second portion of the transmitted infrared light based on times of flight of the detected reflections of the first and second portions of the transmitted infrared light;
filtering out ambient infrared light from light detected by the sensor; and
tracking positions of the eye based on filtered outputs of the sensor, by using the detected reflections of the first portion of the transmitted infrared light.

2. A method according to claim 1, wherein said transmitting infrared light from the first source comprises transmitting infrared light from the first source during a first shutter window in each of a plurality of sequential imaging frames; and
wherein the first source does not transmit during a second shutter window in each of the plurality of sequential imaging frames, and wherein the first and second shutter windows do not overlap;
the method further comprising:
transmitting infrared light from a second source during a third shutter window in each of the plurality of sequential imaging frames, wherein the first source does not transmit during the third shutter window and the second source does not transmit during the first shutter window, in each of the plurality of sequential imaging frames;
identifying the ambient energy in the environment based on a difference between energy detected by the sensor during the first shutter window and energy detected by the sensor during the second shutter window, in each of the plurality of imaging frames;
distinguishing energy detected by the sensor during the first shutter window from energy detecting by the sensor during the third shutter window, in at least one of the plurality of sequential imaging frames; and
identifying corneal glints from the eye based on a difference between the energy detected by the sensor during the first shutter window and the energy detected by the sensor during the third shutter window, in said at least one of the plurality of imaging frames, wherein said tracking positions of the eye includes using the corneal glints to perform gaze stabilization.

3. A method according to claim 1, further comprising:
using a human-visible spectrum camera to capture images of a scene corresponding to a gaze direction of the person.

4. A method according to claim 1, further comprising:
transmitting light from a second source mounted on eyeglasses.

5. A method according to claim 1, wherein said transmitting comprises controlling the first source to transmit energy during a first shutter window of an imaging frame and not to transmit energy during a second shutter window of the imaging frame; and
wherein said filtering out ambient infrared light from light detected by the sensor comprises identifying ambient infrared light in the environment based on a difference between infrared light detected by a time-of-flight detector during the first shutter window and infrared light detected by the time-of-flight detector during the second shutter window.

6. A method according to claim 5, wherein the first and second shutter windows do not overlap.

7. A method according to claim 5, further comprising:
controlling a second source to transmit energy during a third shutter window of the imaging frame;
wherein the first source does not transmit during the third shutter window and the second source does not transmit during the first shutter window.

8. A method according to claim 7, further comprising:
distinguishing energy detected by the sensor during the first shutter window from energy detecting by the sensor during the third shutter window; and
identifying corneal glints from the eye based on a difference between the energy detected by the sensor during the first shutter window and the energy detected by the sensor during the third shutter window.

9. A method according to claim 1, further comprising:
detecting corneal glints; and
performing gaze stabilization based on the detected corneal glints.

* * * * *